United States Patent [19]
Schofield

[11] Patent Number: 4,889,804
[45] Date of Patent: Dec. 26, 1989

[54] BIOCHEMICAL PREPARATION OF ALKENE DERIVATIVES

[75] Inventor: John A. Schofield, Sittingbourne, United Kingdom

[73] Assignee: Shell Oil Company, Houston, Tex.

[21] Appl. No.: 135,212

[22] Filed: Dec. 21, 1987

[30] Foreign Application Priority Data

Jan. 1, 1987 [GB] United Kingdom ................. 8700462

[51] Int. Cl.$^4$ ........................... C12P 7/02; C12R 1/40
[52] U.S. Cl. .................................. 435/155; 435/156; 435/253.3; 435/877
[58] Field of Search ..................... 435/155, 156, 253.3, 435/877

[56] References Cited

U.S. PATENT DOCUMENTS 4,508,822 4/1985 Taylor ................................ 435/155

FOREIGN PATENT DOCUMENTS 76606 4/1983 European Pat. Off. .

OTHER PUBLICATIONS

Katsuhisa Shirai et al., *Agric. Biol. Chem.*, 43(7), pp. 1399–1406, 1595–1596, 1979.

*Primary Examiner*—Herbert J. Lilling
*Attorney, Agent, or Firm*—Nancy J. Gracey

[57] ABSTRACT

Certain novel alkenyl-substituted dihydroxycyclohexadienes and the corresponding catechols are prepared by providing a culture of a microorganism selected from *P.putida* NCIB 12190 and mutants thereof, supplying to the culture the corresponding benzene derivatives in suitable fermentation medium, and subsequently recovering the desired dihydroxycyclohexadiene in cis-relationship, optionally followed by dehydrogenating the compound to afford the corresponding catechol.

16 Claims, No Drawings

BIOCHEMICAL PREPARATION OF ALKENE DERIVATIVES

FIELD OF THE INVENTION

This invention relates to a biochemical process for the preparation of certain alkenyl-substituted dihydroxycyclohexadienes and catechols from alkenyl-substituted benzenes, and to novel alkenyl-substituted dihydroxycyclohexadienes and catechols.

DESCRIPTION OF THE STATE OF THE ART

The conversion of styrene into phenylethyl alcohol by Pseudomonas species is known from several references, for example, from Katsuhisa et al, *Agric. Biol. Chem.*, 43(7), pp. 1399–1406 and 1595–1596 (1979). It is to be noted that this conversion involves attack on the vinyl group in the styrene molecule, not on the benzene ring.

European Patent Application publication number EP-A-No. 76606 discloses a process for the production of a compound comprising a 1,2-dihydroxycyclohexa-3,5-diene ring which process comprises supplying an aromatic compound and an energy source to a mutant strain of Pseudomonas putida in a medium which supports little or no growth of the cells of the mutant strain. It further states that the aromatic compound may have one or more substituents, which substituents may be hydrocarbyl groups, having one to four carbon atoms, e.g., methyl, ethyl, or vinyl and/or heteroatoms or hetero-groups, e.g., halogen. However, the specification does not contain any examples of the process employing a vinyl-substituted aromatic compound and there is no indication that the vinyl group itself would survive the process.

We have surprisingly found that certain alkenyl-substituted benzenes can be converted by certain strains of Pseudomonas putida (hereinafter *P.putida*) to produce alkenyl-substituted dihydroxycyclohexadienes, and that such compounds are substantially resistant to attack by the microorganism on the alkenyl substituent.

SUMMARY OF THE INVENTION

Accordingly, the invention provides a biochemical process for the preparation of a compound of formula

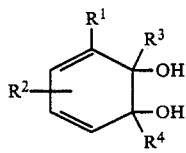
(I)

in which $R^1$ is an alkenyl group having up to four carbon atoms, $R^2$ is a hydrogen atom, a halogen atom or an alkyl group having up to four carbon atoms, and $R^3$ and $R^4$ are hydrogen atoms in cis-relationship or $R^3$ and $R^4$ jointly form a single chemical bond, which comprises preparing a culture of a microorganism selected from *P.putida* NCIB 12190 and mutants thereof, supplying to the culture a compound of formula

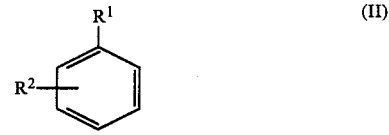
(II)

in which $R^1$ and $R^2$ are as defined previously in a suitable fermentation medium, and subsequently recovering a compound of formula (I) in which $R^3$ and $R^4$ are both hydrogen atoms in cis-relationship, optionally followed by dehydrogenating the compound of formula (1) to afford a compound of formula (I) in which $R^3$ and $R^4$ jointly form a single chemical bond.

Preferably $R^1$ is a vinyl group and $R^2$ is a hydrogen atom.

*P.putida* NCIB 12190 was deposited on Dec. 6, 1985, with the National Collection of Industrial Bacteria, Torry Research Station, Aberdeen, Scotland. The isolation of this type of microorganism has been described by Axcell and Geary, *Biochem. J.*, 146, pp. 173-183 (1975) and *Biochem. J.*, 136, pp. 927-934 (1973).

*Pseudomonas putida* NCIB 12190 has been characterised and identified by the NCIB as follows:

Tests were at 25° C. and growth was on LAB M Nutrient Agar unless otherwise stated.
Cell Morphology
After growth for 24 hours at 30° C. on succinate agar and transfer to Nutrient broth+0.75% w agar, by phase contrast at×630 magnification the cells are small short rods or cocci in clusters.
Gram Negative
Spores —
Motility +
Colonial Morphology
After 48 hours growth, colonies are round, regular, entire, smooth, opaque, low convex, off-white and less than 1 mm in diameter.
Growth in Glucose Peptone Water Sugars
    37° C. +
    41° C. —
Catalase +
Oxidase, Kovac +
O-F glucose Oxidative
"O-F glucose" was performed using the oxidation-fermentation medium of Hayward and Hodgkiss, *J. Gen. Microbiol.*, 26, (1961), pp. 133–140, supplemented with 1% w filter-sterilised D-glucose. A tube sample was inoculated and incubated for 14 days.

*Pseudomohas putida* NCIB 12190 can conveniently be stored on nutrient agar slopes at 4° C., or as a freeze-dried material.

The UV mutant of *Pseudomonas putida* NCIB 12190 described in Example 1 had the same characteristics as those described above, with the exception of motility-negative.

Suitable mutants are those obtained using chemical mutagenesis (such as by use of N-methyl-N'-nitro-N-nitrosoguanidine) or by physical methods (such as by use of ultraviolet radiation). Suitable mutants and selection procedures are described in our British Patent Application No. 8616613 and its equivalent U.S. patent application Ser. No. 068,493, filed July 1, 1987, the disclosures of which are incorporated herein by reference.

The culture of *P.putida* or the mutant strain may be initially grown in the presence of any suitable carbon source. However, a preferred carbon source capable of producing a constitutive culture for the desired biochemical process is, e.g., citric acid, fumaric acid, or succinic acid and the like, suitably in the form of an alkali or alkaline earth metal salt, such as disodium succinate. Other similar, but less expensive, carbon sources are those derived from citric acid and fumaric acid, e.g., trisodium citrate and disodium fumarate or equivalent materials suitable as a carbon source.

The use of such carbon sources as, for example, salts of succinic, citric and fumaric acid, is particularly useful in that the grown *P.putida,* even when using the wild type strain, is found to be constitutive for the dioxygenase required for the process.

The fermentation medium employed is selected to optimize the yield of the compound of formula (I). However, the fermentation medium preferably contains salts of succinic, citric or fumaric acid, as described above for the initial carbon source. Conveniently the fermentation medium is capable of supporting the growth of the culture and may be, for example, the medium in which the culture was prepared.

The product compounds may be recovered from the resulting fermentation broth by any suitable means, such as adsorption onto granulated charcoal, followed by stripping with a suitable solvent with further purification as necessary dependent on the intended use of the product. Alternative recovery means include solvent extraction, for example, using ethyl acetate, dichloromethane or diethyl ether.

When it is desired to perform the optional step of dehydrogenating a compound of formula (I) in which $R^3$ and $R^4$ are hydrogen atoms in cis-relationship to afford a compound of formula (I) in which $R^3$ and $R^4$ jointly form a single chemical double bond, this may be effected using a microorganism or a chemical catalyst.

A suitable microorganism which may be used to effect the optional dehydrogenation step in the process according to the invention is a mutant strain of a benzene-metabolizing microorganism which mutant strain contains a cis-benzene glycol dehydrogenase and is capable of accumulating the required compound of formula (I) where $R^3$ and $R^4$ jointly form a single chemical bond. Thus the dehydrogenation step may be effected by supplying to a culture of the mutant strain containing a cis-benzene glycol dehydrogenase in a suitable fermentation medium a compound of formula (I) in which $R^3$ and $R^4$ are hydrogen atoms in cis-relationship and subsequently recovering therefrom a compound of formula (I) in which $R^3$ and $R^4$ jointly form a single bond.

Preferably the mutant strain containing a cis-benzene glycol dehydrogenase has been obtained by mutating a wild type strain of *P.putida.* A preferred wild type strain is *P.putida* NCIB 12190, described hereinbefore.

Suitable mutant strains containing a cis-benzene glycol dehydrogenase may be obtained using chemical mutagenesis (such as by use of N-methyl-N'-nitro-N-nitrosoguanidine) or physical methods (such as by use of ultraviolet radiation). Suitable mutants and selection procedures are described in our above-mentioned British Patent Application No. 8616613.

When it is desired to effect the optional dehydrogenation step in the process according to the invention using a chemical catalyst, the chemical catalyst may be a palladium or platinum catalyst, for example, palladium or platinum on charcoal. Preferably the process is effected in the presence of gaseous oxygen and an organic solvent.

Compounds of formula (I) have applications as chemical intermediates, for example, in the preparation of polymers. Thus compounds of formula (1) in which $R^3$ and $R^4$ are both hydrogen atoms in cis-relationship may be dehydrated to the corresponding 2- and 3-vinylphenols. Vinyl phenols can be polymerized to give products which after methylolation, for example, in water or organic solvent and with an alkaline catalyst, are suitable for use in resins, paints and adhesives. Compounds of formula (I) in which $R^3$ and $R^4$ together form a single chemical bond can be methylolated in an analogous manner to give polymeric products of similar utility.

The following example illustrates the invention and should not be regarded as limiting it in any way.

| Example 1 | |
|---|---|
| Preparation of Cis-1,2-Hydroxy-3-Vinyl-Cyclohexa-3,5-Diene Using a Mutant of *P. putida* NCIB 12190 | |
| (a) Nutrient solution | |
| Yeast extract | 3 g |
| Disodium succinate.6H$_2$O | 10 g |
| (NH$_4$)$_2$SO$_4$ | 2 g |
| Metals solution | 10 ml |
| 25 mM phosphate buffer, pH7 | 1000 ml |
| (b) Metals solution | |
| CaCl$_2$.2H$_2$O | 125 mg |
| MnSO$_4$.4H$_2$O | 25 mg |
| ZnSO$_4$.7H$_2$O | 25 mg |
| Water | 100 ml |
| (c) Peptone solution | |
| MgSO$_4$.7H$_2$O | 2 g |
| Bactopeptone (Difco) | 0.2 g |
| Water | 10 ml |
| (d) Isolation of *P. putida* mutant | |

Aliquots of 1 ml of a suspension of *P.putida* NCIB 12190 in phosphate buffer pH 7 were spread onto nutrient agar plates. The plates were irradiated using a chromatolux U.V. lamp for 5 to 30 minutes. The plates were incubated at 30° C. overnight and then placed in an atmosphere of fluorobenzene at 30° C. and incubated for a further hours. Thirty-four surviving colonies were purified and tested for their ability to accumulate fluorocatechol in shake flask experiments. Fluorocatechol was assayed by gas chromatography. In comparative experiments, one mutant strain accumulated 0.56 g/l in 3–4 hours. Under the same conditions the wild strain NCIB 12190 accumulated 0.41 g/l.

Peptone solution (0.1 ml) was added to nutrient solution (50 ml) in a 250 ml conical flask, which was then inoculated with the mutant of *P.putida* isolated as described above and incubated at 30° C. on a shaker for 18 hours. Styrene (0.1 ml) was then added to the flask which was then sealed and incubated at 30° C. for 24 hours. The fermentation broth was extracted with diethyl ether (2×50 ml) and the extract dried with sodium sulphate and evaporated to give a product. The product was analyzed by GLC and the results are tabulated in Table 1 below.

TABLE 1

| Retention Time | Peak Area (GLC Integrated Units) | |
|---|---|---|
| (Min.) (RT) | Crude Product | Crude Product + H |
| 5.96 | 1774 | 15166 |
| 7.63 | 0 | 6740 |
| 8.59 | 34282 | 0 |
| 9.60 | 8294 | 7975 |
| 11.41 | 0 | 20192 |

TABLE 1-continued

| Retention Time | Peak Area (GLC Integrated Units) | |
|---|---|---|
| (Min.) (RT) | Crude Product | Crude Product + H |
| 12.53 | 43474 | 37751 |

(a) RT 5.96 2-vinylphenol

The retention time and mass spectrum were both identical with those of an authentic sample of 2-vinylphenol.

(b) RT 8.59 cis-1,2-dihydroxy-3-vinylcyclohexa-3,5-diene.

The mass spectrum shows a parent ion of m/e=138 which together with the fragmentation pattern and the acid lability of the material (as described below) indicates that the product is cis-1,2-dihydroxy-3-vinylcyclohexa-3,5-diene.

(c) RT 9.60 β-hydroxyacetophenone

The retention time and mass spectrum were both identical with those of an authentic sample of β-hydroxyacetophenone.

(d) RT 12.53 1,2-dihydroxy-1-phenylethane.

The retention time and mass spectrum were both identical with those of an authentic sample of 1,2-dihydroxy-1-phenylethane.

Acid Treatment of the Crude Reaction Product

A small aliquot of the crude reaction mixture was added to 2N sulphuric acid (20 ml) and the mixture was allowed to stand for 18 hours at room temperature. The mixture was then extracted with ether (2×2 ml) and the dried (Na₂SO₄) extract was analyzed by GLC. The results are given in Table 1 above and show as the major feature the total disappearance of RT 8.59 and the formation of RT 5.96, RT 7.63 and RT 11.41. This results from the acid catalyzed dehydration (and aromatization) of the cis-1,2-dihydroxy-3-vinylcyclohexa-3,5-diene to a mixture of 2-vinyl-phenol and 3-vinylphenol.

The mass spectrum of RT 7.63 shows a parent ion of m/e=120 which together with the similarity of its fragmentation pattern to that of RT 5.96 suggests that it corresponds to 3-vinyl-phenol.

The mass spectrum of RT 11.41 shows a parent ion of m/e=138 and a fragmentation pattern similar to that of RT 8.59 but was not fully identified.

What is claimed is:

1. A biochemical process for the preparation of a compound of formula (I)

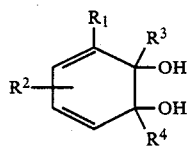
(I)

in which $R^1$ is an alkenyl group having up to four carbon atoms, $R^2$ is a hydrogen atom, a halogen atom or an alkyl group having up to four carbon atoms, and $R^3$ and $R^4$ are hydrogen atoms in cis-relationship, which comprises preparing a culture of a microorganism selected from P. putida NCIB 12190 and mutants thereof; supplying to the culture a compound of formula (II)

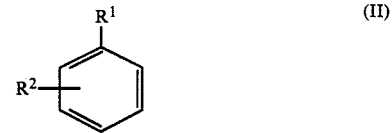
(II)

in which $R^1$ and $R^2$ are as defined previously in suitable fermentation medium and subsequently recovering a compound of formula (I) in which $R^3$ and $R^4$ are both hydrogen atoms in cis-relationship.

2. A process according to claim 1, in which $R^1$ is a vinyl group and $R^2$ is a hydrogen atom.

3. A process according to claim 1, in which the culture is prepared in the presence of a carbon source capable of producing a culture constitutive for the enzyme required.

4. A process according to claim 3, in which the carbon source is succinic, citric or fumaric acid.

5. A process according to claim 1, in which the fermentation medium comprises a salt of succinic, citric or fumaric acid.

6. A process according to claim 1, in which the fermentation medium is capable of supporting the growth of the culture.

7. A process according to claim 1, in which the organism is wild type P.putida NCIB 12190.

8. A process according to claim 1, in which the microorganism is a U.V. mutant of P.putida NCIB 12190.

9. A process according to claim 1 wherein the resulting compound of formula (I) is substantially dehydrogenated to a compound of formula I in which $R^3$ and $R^4$ jointly form a single chemical bond.

10. A process according to claim 9, in which dehydrogenation is effected by a mutant strain of the microorganism P.putida NCIB 12190 which mutant strain contains a cis-benzene glycol dehydrogenase and is capable of accumulating the desired compound of formula (I) in which $R^3$ and $R^4$ jointly form a single chemical bond.

11. A process according to claim 10, in which the mutant strain containing a cis-benzene glycol dehydrogenase has been obtained by mutating a wild type strain of Pseudomonas putida.

12. A process according to claim 11, in which the wild type strain is P.putida NCIB 12190.

13. A process according to claim 9, in which dehydrogenation is effected by a metal catalyst selected from palladium and platinum.

14. A process according to claim in which dehydrogenation is effected in the presence of gaseous oxygen and an organic solvent.

15. A process according to claim 10, in which the fermentation medium comprises molasses or a salt of succinic, citric of fumaric acid.

16. A process according to claim 8, in which the mutant strain is a U.V. mutant of P.putida NCIB 12190.

* * * * *